(12) United States Patent
Niezgoda et al.

(10) Patent No.: US 8,092,575 B2
(45) Date of Patent: Jan. 10, 2012

(54) CONTROL METHODS FOR TRACKING FILTER LIFE IN AN AIR TREATMENT SYSTEM

(75) Inventors: Thomas A. Niezgoda, Kentwood, MI (US); Thomas J. Leppien, Grand Haven, MI (US); Gregory K. Evans, Grand Rapids, MI (US)

(73) Assignee: Access Business Group International LLC, Ada, MI (US)

( * ) Notice: Subject to any disclaimer, the term of this patent is extended or adjusted under 35 U.S.C. 154(b) by 74 days.

(21) Appl. No.: 12/582,769

(22) Filed: Oct. 21, 2009

(65) Prior Publication Data

US 2010/0037769 A1  Feb. 18, 2010

Related U.S. Application Data

(62) Division of application No. 11/456,955, filed on Jul. 12, 2006, now Pat. No. 8,021,469.

(60) Provisional application No. 60/699,163, filed on Jul. 14, 2005.

(51) Int. Cl.
*B01D 46/30* (2006.01)
(52) U.S. Cl. .......... 95/26; 95/1; 96/417; 96/422; 96/423
(58) Field of Classification Search ................. 96/417, 96/422, 423; 95/1, 26
See application file for complete search history.

(56) References Cited

U.S. PATENT DOCUMENTS

| | | | |
|---|---|---|---|
| 3,826,180 A | 7/1974 | Hayashi | |
| 5,036,462 A | 7/1991 | Kaufman et al. | |
| 5,074,137 A | 12/1991 | Harris et al. | |
| 5,477,218 A | 12/1995 | Manmoto et al. | |
| 5,800,583 A * | 9/1998 | Pippel et al. | 55/467 |
| 6,030,437 A * | 2/2000 | Gourrier et al. | 96/399 |
| 6,391,102 B1 * | 5/2002 | Bodden et al. | 96/417 |
| 6,605,131 B2 * | 8/2003 | Vanderveen et al. | 95/11 |
| 2001/0045159 A1 * | 11/2001 | Johnson et al. | 95/26 |

(Continued)

FOREIGN PATENT DOCUMENTS

WO  2004110593  12/2004

OTHER PUBLICATIONS

Webster's New World Computer Dictionary (2003).*

(Continued)

*Primary Examiner* — Jason M Greene
*Assistant Examiner* — Anthony Shumate
(74) *Attorney, Agent, or Firm* — Warner Norcross & Judd LLP

(57) ABSTRACT

A control system and associated methods for an air treatment system. In one aspect, the present invention provides a control system and method for controlling blower speed as a function of separately determined smoke and dust concentrations. In one embodiment, the control system and method provides a variable delayed between changes in motor speed to address undesirable rapid changes between speeds. In another aspect, the present invention provides a system and method for calibrating a sensor to provide more uniform operation over time. In yet another aspect, the present invention provide a system and method for calibrating motor speed to provide more consistent and uniform motor speed over time. The present invention also provides a system and method for tracking filter life by as a function of time, motor speed and/or a sensed variable, such as particulate concentration in the environment.

18 Claims, 7 Drawing Sheets

U.S. PATENT DOCUMENTS

2004/0205697 A1* 10/2004 Hylands et al. ............... 717/106
2005/0060974 A1* 3/2005 Palmerton et al. .............. 55/482
2006/0265149 A1* 11/2006 Palmerton et al. .............. 702/45
2006/0278086 A1 12/2006 Inagaki et al.
2008/0129529 A1 6/2008 Ford et al.

OTHER PUBLICATIONS

Dictionary of Computing. (2008).*
Sharp Electronics Corp., "Use of Optical Sensor Units", 2005, Chapter 12, pp. 12-1-12-20.

* cited by examiner

US 8,092,575 B2

CONTROL METHODS FOR TRACKING FILTER LIFE IN AN AIR TREATMENT SYSTEM

The present application is a divisional of U.S. patent application Ser. No. 11/456,955, filed Jul. 12, 2006, which claims the benefit of U.S. Provisional Application No. 60/699,163 filed Jul. 14, 2005.

BACKGROUND OF THE INVENTION

The present invention relates to control systems and methods, and more particularly to control systems and methods for an air treatment system.

Air treatment systems are available with a wide variety of control systems. A number of air treatment systems include manual control systems that permit the user to manually control a variety of aspects of operation of the system, such as motor speed and time of operation. This permits the user to manually increase the motor speed in response to environmental conditions, for example, when cigarette smoke enters the room. Some of the more complex control systems provide automation of select operation, including motor speed and time of operation. For example, some control systems have the ability to adjust the motor speed in response to smoke and particulate concentrations in the air. This eliminates the need for the user to continually adjust the air treatment system to match environmental conditions.

Over time, conventional filters become increasingly filled with contaminants filtered from the air. The accumulation of contaminants increasingly affects performance of the air treatment system. At some point, the filter reaches a condition where it should be replaced. To assist a user in determining the appropriate time for filter replacement, some air treatment systems have the ability to track usage and calculate an approximation of when the filter should be replaced. Typically, these types of systems provide a visual indication, such as an illuminated LED, when it is time to change the filter. Although an improvement over systems without the ability to track filter life, conventional control systems of this type oversimplify the factors that contribute to filter life, and accordingly may not provide a particularly accurate approximation of filter life.

Although existing control system help to automate operation of the air treatment system, there remains a need for a more efficient and effective control system that is capable of taking into consideration a wide variety environmental conditions. This need also extends to control systems with more accurate and effective ways of tracking filter life.

SUMMARY OF THE INVENTION

In one aspect, the present invention provides a system for automatically controlling the blower speed of an air treatment system in response to separately determined smoke and dust concentrations.

In another aspect, the present invention provides a system for providing variable delayed control over motor speed during the automatic mode of operation.

In yet another aspect, the present invention provides a system for calibrating a particulate or chemical sensor incorporated into an air treatment system.

In a further aspect, the present invention provides a system for calibrating blower motor speed.

In another aspect, the present invention provides a system for tracking filter life as a function of time, blower speed and/or a sensed variable, such as particulate concentration or total particulates accumulated in the filter.

These and other objects, advantages, and features of the invention will be readily understood and appreciated by reference to the detailed description of the current embodiment.

DESCRIPTION OF THE CURRENT EMBODIMENT

Figure 1:
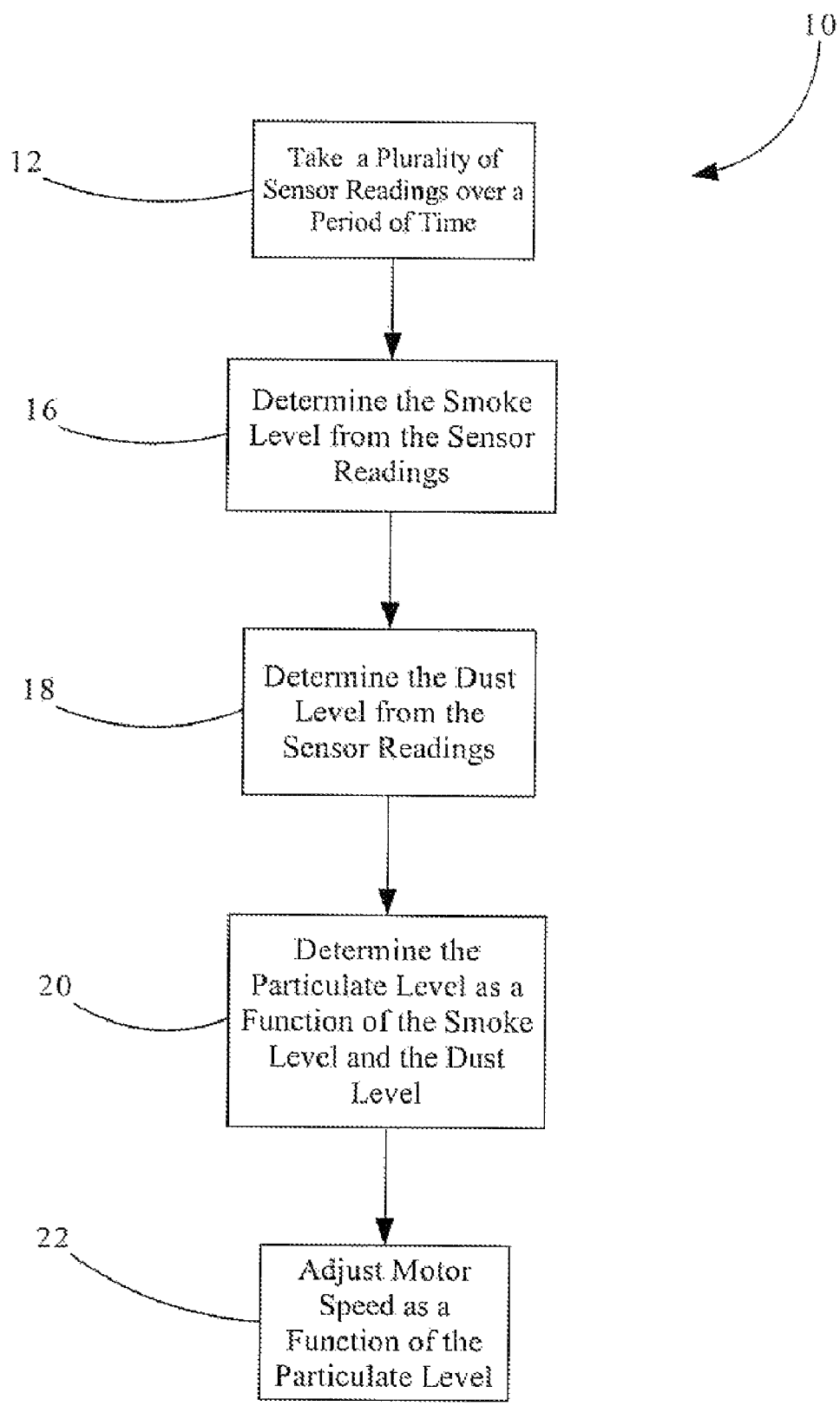
FIG. 1 is a flowchart showing the general steps of one embodiment of the automatic motor speed control algorithm.

The present invention is described in connection with an air treatment system having a blower that moves air through a prefilter, a particulate filter and an odor filter. The air treatment system includes a control system that monitors and controls operation of the system. The control system includes generally conventional components, such as a programmable microcontroller and one or more sensors. In one embodiment, the control system includes a particulate sensor that provides information concerning the amount of particulate matter in the air, as well as an RPM sensor that provides information concerning the speed of the blower motor.

The microcontroller is configured to run a plurality of control algorithms and to receive input from the sensors. In summary, the control system may include an automatic operation algorithm that automatically adjusts blower motor speed as a function of the output of the particulate sensor. The automatic control algorithms may utilize separate smoke and dust level algorithms to determine blower motor speed. The control system may also include a variable delay algorithm for permitting the user to control the minimum amount of time that the blower will remain at a given speed before permitting adjustment to a different speed. The control system may further include calibration algorithms that improve the performance of the system. In one embodiment, the calibration algorithms include a particulate sensor calibration algorithm that can be run to calibrate the particulate sensor during production and periodically during operation. The calibration algorithms may also include a motor calibration algorithm that can be run to provide ongoing calibration of blower motor speed. The control system may further include algorithms for tracking the life of the prefilter, odor filter and particulate filter. The control filter life algorithms may track filter life based on time, blower speed, total amount of particulate entering the system and/or particulate concentration, and may take appropriate action, such as illuminate an indicator, when it is necessary to clean or replace a filter.

The following sections described the aforementioned control algorithms in detail.

I. Automatic Motor Speed Control.

In one aspect, the present invention provides an algorithm for automatically controlling the speed of a blower motor in an air treatment system as a function of a sensed variable. For example, in one embodiment, the system automatically increases or decreases the blower motor speed as a function of the amount of particulates sensed by a particulate sensor. In this embodiment, the blower motor may be moved between five discrete motor speeds. The number of different motor speeds may be varied from application to application as desired. In one embodiment, the blower motor speed is adjusted by varying the percent duty cycle of the speed control signal supplied to the blower motor using conventional techniques and apparatus.

In this embodiment, the air treatment system includes a generally conventional particulate sensor having an output voltage that varies depending on the amount of particulate matter in the air. One suitable particulate sensor is available from Sharp as Part No. GP2Y1010AU. This particular sensor includes an LED spaced apart from a light sensor. The light sensor is configured to provide a signal having a voltage that is proportional to the amount of light emitted by the LED that reaches the sensor. The sensor is configured so that light emitted by the LED does not have a direct path to the light sensor. Rather, the LED light will only reach the sensor if it is reflected toward the sensor. Particles in the air provide the reflection necessary to direct some of the LED light toward the light sensor. The greater the size and/or number of particles in the air, the greater the amount of light that will be reflected to the sensor and hence the greater the output voltage. The particle sensor provides an analog signal, and may be connected to an analog input on the microcontroller. The microcontroller may convert the analog signal to a corresponding digital signal for processing.

As noted above, the control system is configured to operate the blower motor at one of five different blower motor speeds. To provide direct correlation between the particulate sensor readings and different blower motor speeds, the range of possible sensor readings is divided into 5 subranges. The number of subranges can vary depending on the number of desired blower speeds. For example, if 3 blower speeds were desired, the range of possible sensor readings would be divided into 3 separate subranges. The method for determining the subranges may vary from application to application. In addition, the correlation of speeds to subranges may vary. For instance, there could be two speeds for each subrange. In this embodiment, however, the subranges are determined by simply dividing the range of possible sensor readings into 5 even subranges. The subranges may alternatively be weighted or otherwise represent unequal portions of the overall range. An example of an alternative method for determining the subranges is described below.

In one embodiment, the control algorithm 10 takes periodic readings from the particulate sensor at a specific rate 12 (See FIG. 1). For example, in one embodiment, the control software takes a reading from the particulate sensor once every 50 milliseconds. The frequency of the readings may vary from application to application. In fact, as described in more detail below, the frequency may be varied as a mechanism to calibrate the sensor output.

In one embodiment, the present invention determines 20 the particulate level from the periodic sensor readings using two different algorithms-one configured to measure the level of smoke in the air 16 and the other configured to measure the level of dust in the air 18. The particulate level can be used to set blower motor speed 22 and may also be displayed to the user. It has been determined that smoke has a more moderate, but consistent, impact on the output of the particle sensor. Particles such as dust, on the other hand, cause more peaks in the output of the particle sensor. Improved performance is provided by determining the particulate level, and consequently the blower motor speed, as a function of both the smoke level and the dust level.

Figure 2:
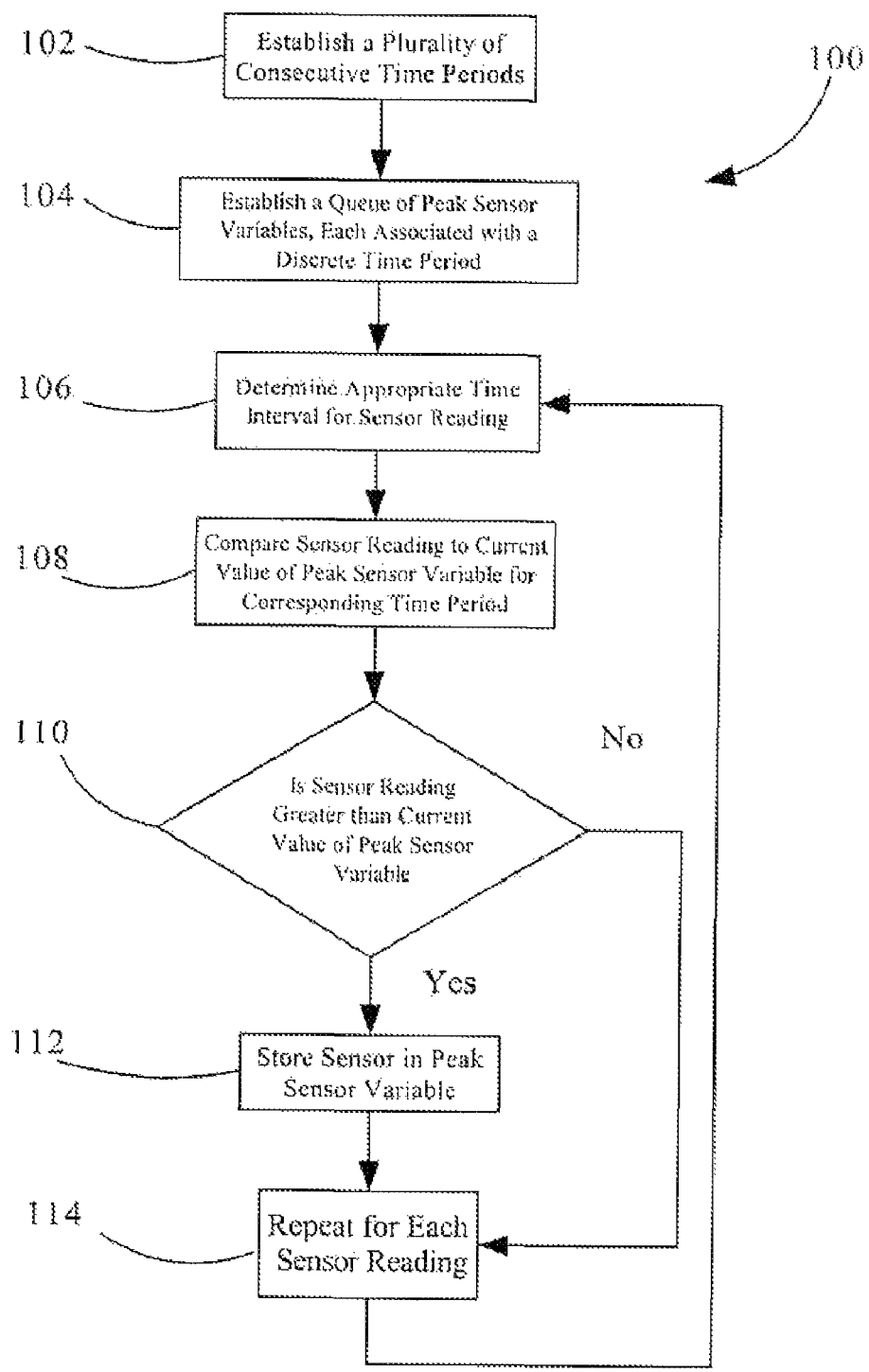
FIG. 2 is a flowchart showing the general steps of one embodiment of the dust algorithm.

In general, the dust algorithm 100 operates by considering a collection of peak sensor readings over a plurality of consecutive time periods 102 (See FIG. 2). The algorithm compares these peak sensor readings to a look-up table to determine the particle level output. In this embodiment, the dust algorithm maintains 104 a revolving first-in-first-out (FIFO) queue of variables, each associated with a discrete time segments. Each of these time segments is referred to as a "bucket." There are six buckets in this embodiment, but the number of buckets may vary from application to application. Each bucket is associated with a fixed time period, which in one embodiment is a ten second interval. But, the length of this interval may vary from application to application. The algorithm uses the aforementioned FIFO queue of variables to maintain a separate peak value for each bucket (or ten second interval). Accordingly, the six buckets are collectively associated with the last 60 seconds and the peak value variable for each bucket contains the highest sensor reading taken during the corresponding bucket (or ten second time interval). Operation of the dust algorithm will now be described in more detail. As noted above, the control system takes a sensor reading every 50 milliseconds. After each reading is taken, the algorithm determines 106 the appropriate bucket using conventional timing techniques, such as using interrupts to maintain a clock. The sensor reading is compared 108 to the current value contained in the peak value variable for the appropriate bucket. If the sensor reading is higher than the current value of the peak value variable 110, then the sensor reading is stored 112 in the peak value variable-overwriting the existing value. If not, the sensor reading is ignored and the existing value is retained. The process repeats 114 for each sensor reading. After the end of each ten second interval, the peak value variable for the associated bucket holds the peak value for that ten second interval and processing continues for the next bucket. As time passes to each new bucket, the sensor readings are considered for writing to the peak value variable for the new bucket. Once six buckets are completed (in other words, the FIFO queue is full), the algorithm overwrites the peak value variable for the oldest of the six buckets. The process continues with each new bucket utilizing the peak value variable for the remaining oldest bucket. As a result, the dust algorithm builds and maintains a queue of six peak value variables that contain the highest sensor readings for each of the immediately preceding six ten second intervals.

Figure 3:
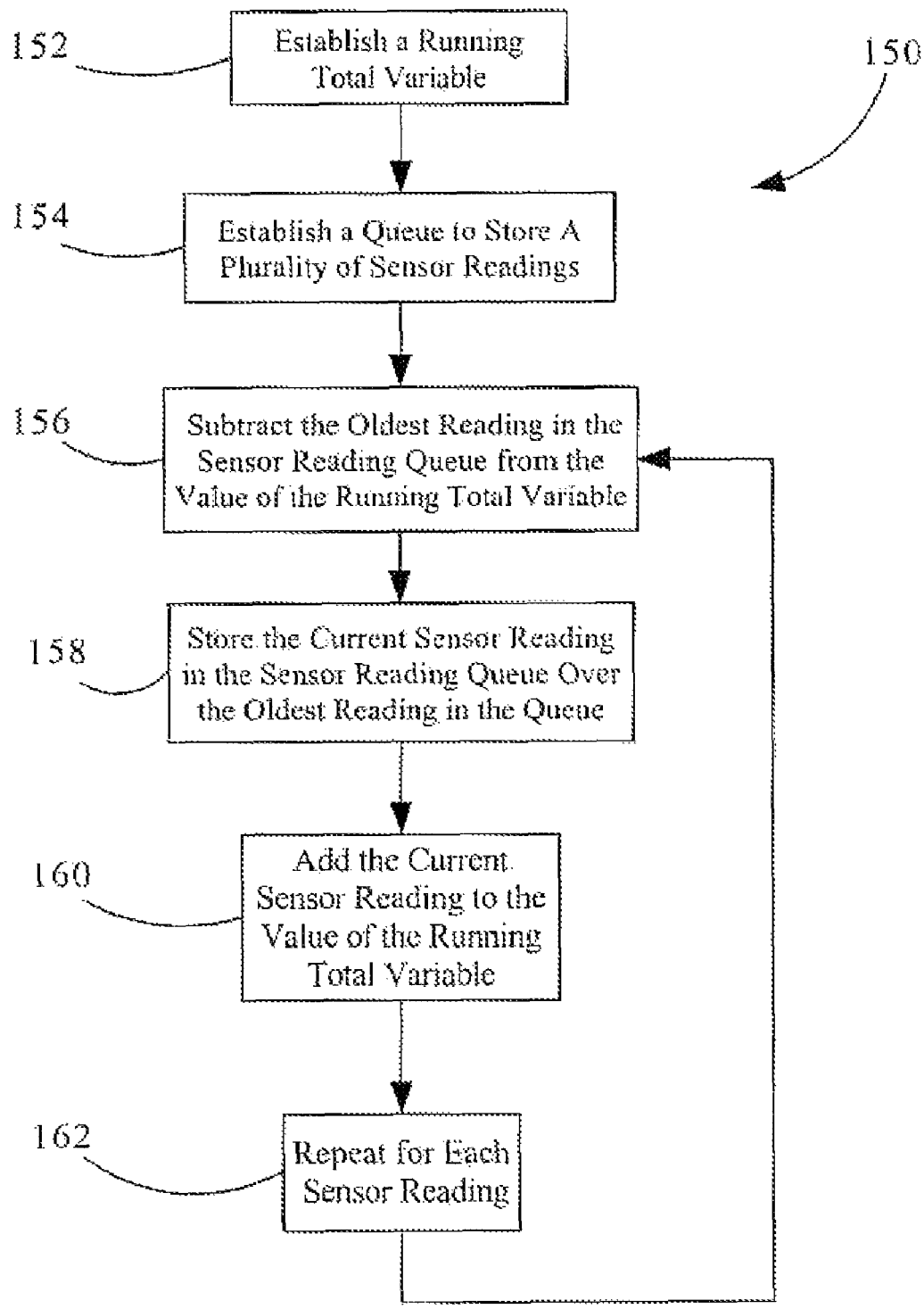
FIG. 3 is a flowchart showing the general steps of one embodiment of the smoke algorithm.

The smoke algorithm 150 separately evaluates the same 50 millisecond sensor readings, but it does so in a different manner (See FIG. 3). The smoke algorithm maintains a rolling average of the readings over a fixed number of readings. For example, in one embodiment, the smoke algorithm 150 maintains a rolling average of the last 100 sensor readings. The 100 readings are maintained in a revolving first-in-first-out (FIFO) buffer 154. At the same time, a running total 152 of the readings contained in the buffer is maintained. Each time a new reading is taken 162, the oldest value in the buffer is subtracted 156 from the total. The new reading is stored over the oldest value in the buffer 158 and the new reading is added to the running total 160. Accordingly, the average of the 100 sensor readings in the buffer can be readily computed by dividing the running total by 100.

Figure 4:
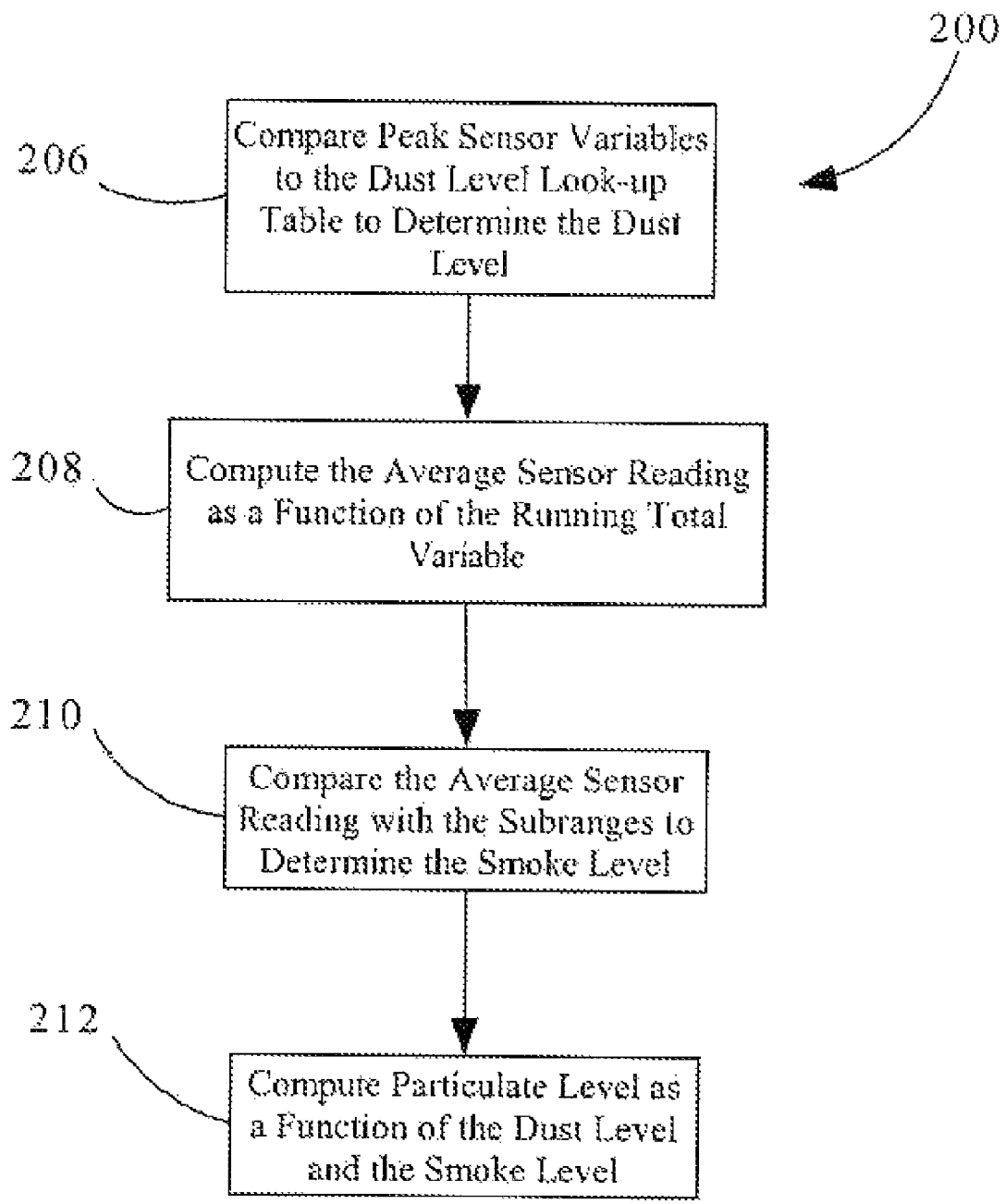
FIG. 4 is a flowchart showing the general steps of one embodiment of the particulate level determination algorithm.

In this embodiment, the data maintained by the smoke algorithm and the dust algorithm is used to compute the overall "particulate level." The particulate level is then used to control blower motor speed. The automatic control algorithm of this embodiment periodically processes the data maintained by the dust algorithm and the smoke algorithm to determine the particulate level. In this embodiment, the data is processed every five seconds. One embodiment of the algorithm 200 for determining the particulate level is shown in FIG. 4. At each five second interval, the automatic control algorithm processes the smoke algorithm data by retrieving the running total of the last 100 samples and dividing that number by 100 to obtain the average sensor reading 208. The average sensor reading is then compared 210 to the five particulate level subranges (which, in this embodiment, are the same as the dust level subranges) to obtain the smoke level. The automatic control algorithm processes the dust algorithm data by performing actions on the six peak dust level variables maintained by the dust algorithm to determine a dust level. In this embodiment, the value contained in each of the six peak dust level variables is separately compared 206 to the five dust level subranges to determine the corresponding dust level for each particular bucket. For each dust level, the algorithm maintains a counter that contains the number of the six current buckets that have the corresponding dust level. For example, if the six buckets include three buckets with a peak value in the dust level 4 range, the value of the dust level four counter would be 3. Similarly, if two of the buckets included a peak value in the dust level 3 range, the value of the dust level 3 counter would be 2. Finally, if the last bucket included a peak value in the dust level 5 range, the value of the dust level 5 counter would be 1. For each dust level counter that is not zero, the counter is compared to a look-up table to determine a corresponding "temporary particle level." The automatic control algorithm then determines the particle level as a function of the temporary values returned from the look-up table. For example, the particle level may simply be the largest of the dust levels returned for each bucket. Alternatively, the particle level can be determined as a simple or weighted average of the returned dust level. The following is a temporary particle level look-up table of one embodiment.

The automatic control algorithm then determines the actual particulate level (and consequently the motor blower speed) as a function of the smoke level and the dust level 212. In one embodiment, the algorithm simply takes the larger of the dust level and the smoke level, and uses that value as the particulate level to set the actual blower speed. In other embodiments, the actual blower speed may be some other function of the dust level and the smoke level. For example, the actual blower speed may be a simple or weighted average of the dust level and the smoke level.

In an alternative embodiment, the control system may include a plurality of different look-up tables for use in connection with the dust algorithm, each being configured to reflect a different level of sensitivity. In this alternative embodiment, the user is provided with a mechanism for selecting the look-up table corresponding with the desired level of sensitivity. For example, in one example of this alternative embodiment, the control system may include five alternative temporary particle level look-up tables. The following are five alternative temporary particle look-up tables for one exemplary embodiment of this alternative embodiment. As can be seen, these alternative look-up tables are configured so that each successive table provides an overall increasingly greater response to the sensed values. By permitting a user to select the desired table, the system is capable of accommodating users with different levels of sensitivity.

| TEMPORARY PARTICLE LEVEL LOOKUP TABLE | | | | | | |
|---|---|---|---|---|---|---|
| | 1 Count | 2 Counts | 3 Counts | 4 Counts | 5 Counts | 6 Counts |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_2 | Dust_Level_2 | Dust_Level_2 | Dust_Level_2 | Dust_Level_2 | Dust_Level_2 |
| Dust Level 3 Counter | Dust_Level_2 | Dust_Level_2 | Dust_Level_2 | Dust_Level_3 | Dust_Level_3 | Dust_Level_3 |
| Dust Level 4 Counter | Dust_Level_3 | Dust_Level_3 | Dust_Level_4 | Dust_Level_4 | Dust_Level_4 | Dust_Level_4 |
| Dust Level 5 Counter | Dust_Level_3 | Dust_Level_4 | Dust_Level_4 | Dust_Level_5 | Dust_Level_5 | Dust_Level_5 |

Row = Dust Level
Column = Number of Buckets within each Dust Level

In the above example, the temporary particle levels determined from the look-up table would be "Dust Level 4," "Dust Level 2" and "Dust Level 3." The algorithm returns the highest of these temporary particle levels as the actual particle level. In this case, the algorithm would return a particle level of 4.

| TEMPORARY PARTICLE LEVEL LOOKUP TABLES | | | | | | |
|---|---|---|---|---|---|---|
| | 1 Count | 2 Counts | 3 Counts | 4 Counts | 5 Counts | 6 Counts |
| Sensitivity Level 1 | | | | | | |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_1 | Dust_Level_1 | Dust_Level_2 | Dust_Level_2 | Dust_Level_2 | Dust_Level_2 |
| Dust Level 3 Counter | Dust_Level_2 | Dust_Level_2 | Dust_Level_2 | Dust_Level_2 | Dust_Level_3 | Dust_Level_3 |
| Dust Level 4 Counter | Dust_Level_2 | Dust_Level_2 | Dust_Level_2 | Dust_Level_3 | Dust_Level_3 | Dust_Level_4 |
| Dust Level 5 Counter | Dust_Level_2 | Dust_Level_3 | Dust_Level_3 | Dust_Level_3 | Dust_Level_4 | Dust_Level_5 |
| Sensitivity Level 2 | | | | | | |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_1 | Dust_Level_1 | Dust_Level_2 | Dust_Level_2 | Dust_Level_2 | Dust_Level_2 |
| Dust Level 3 Counter | Dust_Level_2 | Dust_Level_2 | Dust_Level_2 | Dust_Level_3 | Dust_Level_3 | Dust_Level_3 |
| Dust Level 4 Counter | Dust_Level_2 | Dust_Level_3 | Dust_Level_3 | Dust_Level_3 | Dust_Level_4 | Dust_Level_4 |
| Dust Level 5 Counter | Dust_Level_3 | Dust_Level_3 | Dust_Level_3 | Dust_Level_4 | Dust_Level_4 | Dust_Level_5 |
| Sensitivity Level 3 | | | | | | |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_1 | Dust_Level_2 | Dust_Level_2 | Dust_Level_2 | Dust_Level_2 | Dust_Level_2 |
| Dust Level 3 Counter | Dust_Level_2 | Dust_Level_2 | Dust_Level_2 | Dust_Level_3 | Dust_Level_3 | Dust_Level_3 |
| Dust Level 4 Counter | Dust_Level_3 | Dust_Level_3 | Dust_Level_3 | Dust_Level_4 | Dust_Level_4 | Dust_Level_4 |
| Dust Level 5 Counter | Dust_Level_3 | Dust_Level_3 | Dust_Level_4 | Dust_Level_4 | Dust_Level_4 | Dust_Level_5 |

-continued

TEMPORARY PARTICLE LEVEL LOOKUP TABLES

| | 1 Count | 2 Counts | 3 Counts | 4 Counts | 5 Counts | 6 Counts |
|---|---|---|---|---|---|---|
| | | | Sensitivity Level 4 | | | |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_2 | Dust_Level_2 | Dust_Level_2 | Dust_Level_2 | Dust_Level_2 | Dust_Level_2 |
| Dust Level 3 Counter | Dust_Level_2 | Dust_Level_2 | Dust_Level_2 | Dust_Level_3 | Dust_Level_3 | Dust_Level_3 |
| Dust Level 4 Counter | Dust_Level_3 | Dust_Level_3 | Dust_Level_4 | Dust_Level_4 | Dust_Level_4 | Dust_Level_4 |
| Dust Level 5 Counter | Dust_Level_3 | Dust_Level_4 | Dust_Level_4 | Dust_Level_5 | Dust_Level_5 | Dust_Level_5 |
| | | | Sensitivity Level 5 | | | |
| Dust Level 1 Counter | Dust_Level_1 | Dust_Level_1 | Dust_Level_1 | Dust_Level_1 | Dust_Level_1 | Dust_Level_1 |
| Dust Level 2 Counter | Dust_Level_2 | Dust_Level_2 | Dust_Level_2 | Dust_Level_2 | Dust_Level_3 | Dust_Level_3 |
| Dust Level 3 Counter | Dust_Level_2 | Dust_Level_3 | Dust_Level_3 | Dust_Level_3 | Dust_Level_3 | Dust_Level_4 |
| Dust Level 4 Counter | Dust_Level_3 | Dust_Level_3 | Dust_Level_4 | Dust_Level_4 | Dust_Level_4 | Dust_Level_5 |
| Dust Level 5 Counter | Dust_Level_3 | Dust_Level_4 | Dust_Level_4 | Dust_Level_5 | Dust_Level_5 | Dust_Level_5 |

Row = Dust Level
Column = Number of Buckets within each Dust Level

As noted above, the control system is also provided with a mechanism for permitting the user to select one of the various alternative look-up tables. In one embodiment, the control system is configured to cycle through the alternative look-up tables in response to user input on the control panel. For example, in the illustrated embodiment, the user may depress and hold both the "Automatic" and "Timer" buttons on the control panel while the system is plugged-in to initiate the sensitivity selection algorithm. This algorithm cycles to the next alternative look-up tables each time the "Automatic" button is pressed. If the button is pressed when the most sensitive look-up table is selected, the system cycles back down to the least sensitive look-up table. The control system may leave the sensitivity selection algorithm if the "Automatic" button is not pressed for a given period of time. For example, the control algorithm may exit the sensitivity selection algorithm if the "Automatic" button is not pressed for a period of five seconds. The control panel may include a visual indication of the current sensitivity setting. For example, the control panel may include a separate LED for each setting and the appropriate LED may be illuminated to show the current sensitivity.

II. Variable Delay.

In the automatic mode of operation, it is possible that the determined actual blower speed will vary relatively quickly from one blower speed to another. It is possible that a user will be distracted by constant or rapid changes in blower speed. Accordingly, the automatic control algorithm includes a delay algorithm that will maintain the blower at a given blower speed for a minimum period of time. For example, the delay period may be set at 30 seconds so that the blower will remain at a given speed for at least 30 seconds. If the smoke algorithm and the dust algorithm determines that the blower speed should be varied during this initial 30 second delay, the automatic control algorithms will nonetheless maintain the current blower speed until the end of the 30 second period. At the end of the 30 second period, the automatic control algorithm will again permit the blower speed to be adjusted as a function of the smoke algorithm and the dust algorithm. To provide the delay functionality, the control software maintains a counter of the time that has passed since that last blower speed change. Each time the blower speed is changed, this counter is reset to zero. The automatic control algorithm checks this counter before implementing a blower speed change. If the counter is less than 30 seconds, the automatic control algorithm simply ignores the new blower speed setting determined by the smoke and dust algorithms. If the counter is at or above 30 seconds, the automatic control algorithm implements the blower speed change and resets the counter to zero.

In some applications, it may be desirable to vary the amount of delay included in the blower speed control algorithms. For example, when providing demonstrations of the air treatment system, it may be desirable to demonstrate rapid changes in blower speed in response to changes in the particulate concentration in a room. As another example, a user may prefer a longer or shorter delay. To permit the length of the delay to be varied, the control software includes a variable delay algorithm. The variable delay algorithm permits a user to set the time period during which the blower will remain at a given speed. In one embodiment, the variable delay algorithm permits the user to select one of various preset time delays, for example, ranging from five seconds to 55 seconds in ten second intervals. In this embodiment, changes in the delay may be made by actuation of a corresponding "Variable Delay" control button. Alternatively, changes in the delay may be made by depressing a combination of other control buttons, for example, by cycling through the various delay values in response to simultaneous pushes of the "Blower Speed" and "Automatic" control buttons.

In some situations, the dust level may linger around the borderline between two ranges. Vacillation of the dust level above and below the borderline, may cause the control algorithms to continuously increase and decrease the blower motor speed at the fastest rate permitted by the variable delay algorithms. In some applications, it may be undesirable to have such a rapid and repetitive change in blower motor speed. Accordingly, the control algorithms may include an additional delay algorithm that permits the motor speed to be reduced from one level to the next only when the sensor reading is substantially within the next lower range. In one embodiment, the system will only reduce the blower motor speed if the particulate sensor reading is at least 100 millivolts into the next lower range. The particular offset required to permit movement to the next lower blower motor speed may, however, vary from application to application. Although the described embodiment of this algorithm affects only downward movement of the blower motor speed, the algorithm could alternatively affect only upward movement of the blower motor speed or both upward and downward movement.

III. Sensor Calibration Algorithm.

Experience has revealed that not all particle sensors provide the same output voltage in response to the same particulate concentrations in the air. These variations may result from various factors, such as variations in the light emitted by the LED and imperfections in the light sensor. Further, the sensor's output may vary over time, for example, as a result of changes in the operation of the LED or light sensor that naturally occur over the life cycle of the components.

To improve performance, the present invention provides an algorithm for calibrating a particulate sensor. This algorithm permits that sensor to be calibrated during production to accommodate variations resulting from the manufacture of the sensor, as well as periodically over the life of the air treatment system to accommodate variations occurring over the life cycle of the components. In effect, the algorithm may shift and/or scale the output voltage of the sensor to correlate with the desired blower speeds. Once computed, the sensor calibration data may be stored in an EEPROM so that it can be retrieved even if the system loses power. Although the present invention is described in connection with the calibration of a particulate sensor, the calibration algorithms are well suited for use in calibrating other types of sensors, such as chemical sensors.

Figure 5:
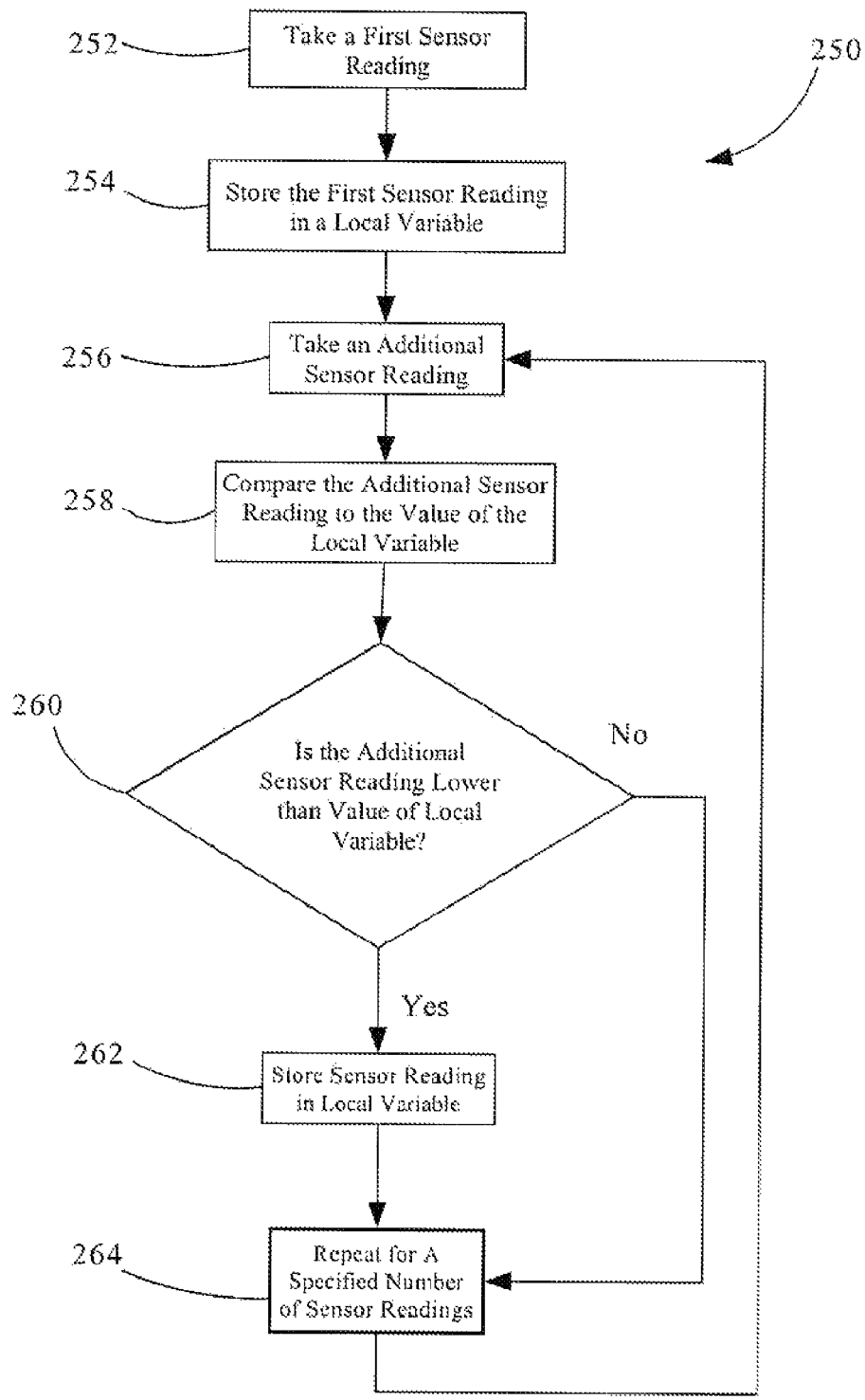
FIG. 5 is a flowchart showing the general steps of one embodiment of the sensor calibration algorithm.

In one embodiment, the calibration algorithm is configured to permit adjustment of the reference voltage (or baseline voltage) (See FIG. 5). The reference voltage is the output voltage expected from the sensor when the particulate concentration is at or reasonably close to zero. To calibrate the reference voltage, the calibration algorithm 250 includes the steps of: (i) taking a first sample reading from the sensor 252, (ii) storing the first sample reading in a local variable 254, (iii) taking a sample reading from the sensor 256, (iv) comparing the reading with the value of the local variable 258, (v) if the reading is lower than the local variable 260, then store the sample reading in the local variable 262, (vi) repeat steps (iii) and (iv) at 100 millisecond intervals until a total of 20 sample readings have been collected 264, and (vii) use the value stored in the local variable as the reference voltage. In an alternative embodiment, the reference voltage may be determined by computing the average of a predetermined number of readings. For example, the control algorithm may include the steps of: (i) taking a first sample reading from the sensor, (ii) storing the first sample reading in a local variable, (iii) taking a sample reading from the sensor, (iv) adding the sample reading to the value of the local variable, (v) repeating steps (iii)-(iv) until a total of 20 samples readings have been taken and the summation of the 20 sample readings is stored in the local variable, (vi) determining the average sample reading by dividing the value stored in the local variable by 20, (vii) using the average sample reading as the reference voltage.

Once the reference voltage has been obtained, the control software can calculate the sensor reading ranges that equate to the possible blower speeds. In this embodiment, the control system is configured to operate the blower motor at five different speeds. Accordingly, the sensor reading ranges are to be divided into five corresponding subranges. In one embodiment, these five subranges are determined by calculating five sequential 250 millivolt windows based on the determined reference voltage. For example, if the reference voltage is determined to be 1.235 volts, the five subranges would be: (1) 1.235 to 1.485 millivolts, (2) 1.486 to 1.736 millivolts, (3) 1.737 to 1.987 millivolts, (4) 1.988 to 2.238 millivolts and (5) 2.239 to 2.489 millivolts. Values falling below 1.235 may be associated with the first subrange. Similarly, values exceeding 2.489 millivolts may be associated with the fifth subrange.

In an alternative embodiment, it may be desirable to vary the size of the subranges. For example, in applications where the output voltage of the sensor is not linearly proportional to the particulate concentration in the air, it may be desirable to vary the size of the subranges to follow the curve of the output voltage. It has been determined that the curve of the output voltage for a given sensor varies based in large part on the output voltage of the sensor when the sensor is sensing substantially clean air (i.e. the reference voltage). In fact, the manufacturer of the particulate sensor identified above and utilized in one embodiment of the present invention provides information about the output voltage curve for the sensors based on the sensor's reference voltage. To adjust the subranges for a given sensor, the algorithm computes the reference voltage for the sensor utilizing the methodology described above. Once the reference voltage is determined, the subrange algorithm uses the reference voltage to determine the subranges. In one embodiment, the subrange algorithm compares the reference voltage to a look-up table stored in the system. The look-up table defines the subranges that correspond with each particular reference voltage. For example, the look-up table may include the values representative of the bounds of each subrange. In an alternative embodiment, the look-up table may be replaced by a formula that approximates the appropriate bounds of each subrange.

There are alternative methodologies for calibrating the sensor. In an alternative embodiment, the calibration algorithm may vary the frequency at which samples are taken from the sensor during normal operation. It has been determined that the sampling frequency affects the output voltage obtained from the sensor. This is true at least with respect to the particulate sensor identified above. The precise reason for this has not been determined, but it appears to be due to inherent characteristics of the sensor. For example, it has been determined that by increasing the sampling frequency there will be a decrease in the output voltage of the sensor over the same air conditions. Similarly, by reducing the sampling frequency there will be an increase in the output voltage of the sensor over the same air conditions. Accordingly, in this embodiment, the calibration algorithm includes the steps of: (i) taking a fixed number of sample readings at a fixed frequency, (ii) comparing the lowest reading value with the desired reference voltage, (iii) if the lowest reading is within an acceptable range for the reference voltage, then quit, leaving the sampling frequency at its current value, (iv) if the lowest reading is higher than the acceptable range, then increase the sampling frequency and repeat steps (i)-(iii), and (v) if the lowest reading is lower than the acceptable range, then decrease the sampling frequency and repeat steps (i)-(iii). In one embodiment, the initial frequency is set to provide a 50 milliseconds interval for sensor readings and the frequency may be adjusted in fixed segments of 5 to 10 millisecond segments. Alternatively, the frequency may be adjusted as a function of the difference between the lowest sample reading and the acceptable range. For example, the frequency may be adjusted by a greater amount if the lowest sample reading is farther away from the acceptable range.

IV. Motor Speed Calibration.

To provide consistent operation of the blower, the present invention provides an algorithm for calibrating motor speed. In one embodiment, the motor speed calibration algorithm is operating continuously to maintain consistent blower operation over the life of the system. In this embodiment, the motor speed calibration algorithm is run each time that the motor speed changes. The motor speed calibration algorithm may alternatively be run continuously or at different times periods.

In one embodiment, the motor includes an RPM sensor that provides a pulse signal at a frequency that is representative of the motor RPMs. The RPM sensor may be connected to a digital input on the microcontroller. The microcontroller may determine the frequency of the PWM signals.

Figure 6:
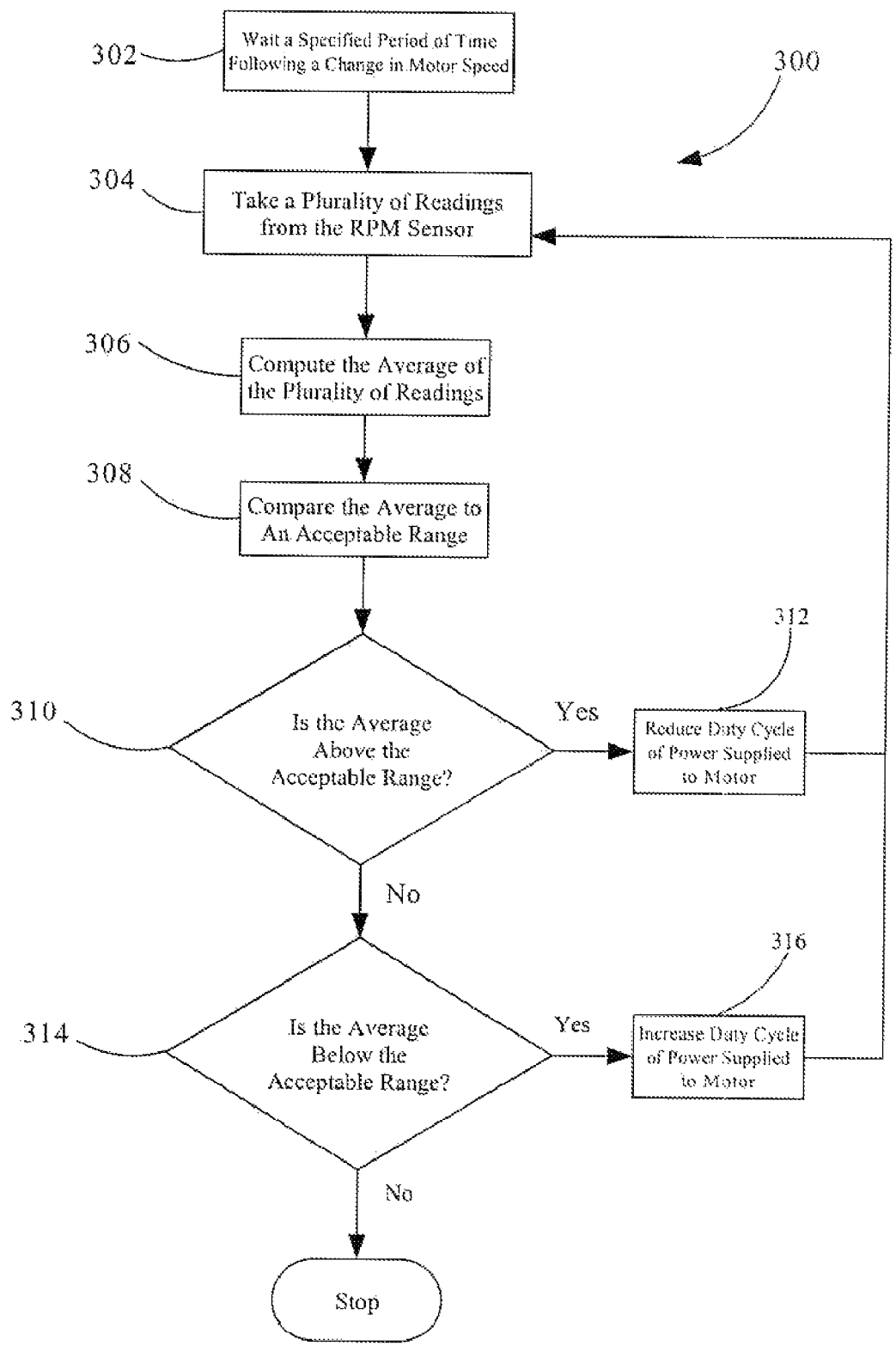
FIG. 6 is a flowchart showing the general steps of one embodiment of the motor speed calibration algorithm.

In one embodiment the motor speed calibration algorithm is run each time that the motor speed is changed. In this embodiment (See FIG. 6), the motor speed calibration algorithm 300 may include the following general steps: (i) wait 30 seconds after a change is blower motor speed 302, (ii) take 30 readings from the RPM sensor at 1 second intervals 304, (iii) compute the average of these 30 readings 306, (iv) compare the average reading with a predetermined range of acceptable RPMs 308, (v) if the average reading is within an acceptable range for that motor speed, then quit, (vi) if the average reading is high 310, the percent duty cycle of the speed control signal applied to the motor is reduced by one percent 312, (vi) if the average reading is low 314, the percent duty cycle of the speed control signal applied to the motor is increased by one percent 316, and (vii) repeat steps (ii) through (vii) until the average reading falls within the acceptable range. If desired, each time there is a change in percent duty cycle, the new value for that particular blower motor speed can be stored in an EEPROM so that the values can be retrieved after the system recovers from a power failure.

As noted, the motor calibration algorithm of one embodiment is run each time the blower motor speed changes. If desired, the system may be configured to provide calibration of all five blower speeds at initial start up. For example, the control system may step through each blower speed upon initial start-up and hence cause calibration at each blower speed.

V. Filter Life.

The present invention includes algorithms for tracking the life of one or more filters. The purpose of these algorithms is to provide the user with an indication when it is necessary to clean or replace the filters. In one embodiment, the present invention is intended for use in an air treatment system having a pre-filter, a particulate filter (e.g. a HEPA filter) and an odor filter (e.g. an activated carbon filter). The present invention includes algorithms for monitoring the life of each of these filters. The life of the pre-filter and the life of the odor filter are computed as a function of time and motor speed. The life of the particulate is computed as a function of time, motor speed and the output of the particulate sensor. In one embodiment, the control system maintains a separate filter life variable for each filter. During operation, these variables are incremented by a value that is determined as a function of the relevant factors (e.g. time, blower speed and/or particulate sensor output).

In one embodiment, the filter life algorithm for the prefilter includes the following general steps: (i) obtain motor speed value, (ii) retrieve corresponding motor speed factor from a pre-filter look-up table, (iii) obtain time interval, (iv) multiply time interval by the motor speed factor, and (v) increment prefilter life counter by the product of time interval and motor speed factor.

In one embodiment, the filter life algorithm for the odor filter is essentially identical to the prefilter algorithm except that it utilizes a different look-up table. The odor filter algorithm includes the following general steps: (i) obtain motor speed value, (ii) retrieve corresponding motor speed factor from the odor filter look-up table, (iii) obtain time interval, (iv) multiply time interval by the motor speed factor, and (v) increment odor filter life counter by the product of time interval and motor speed factor.

Figure 7:
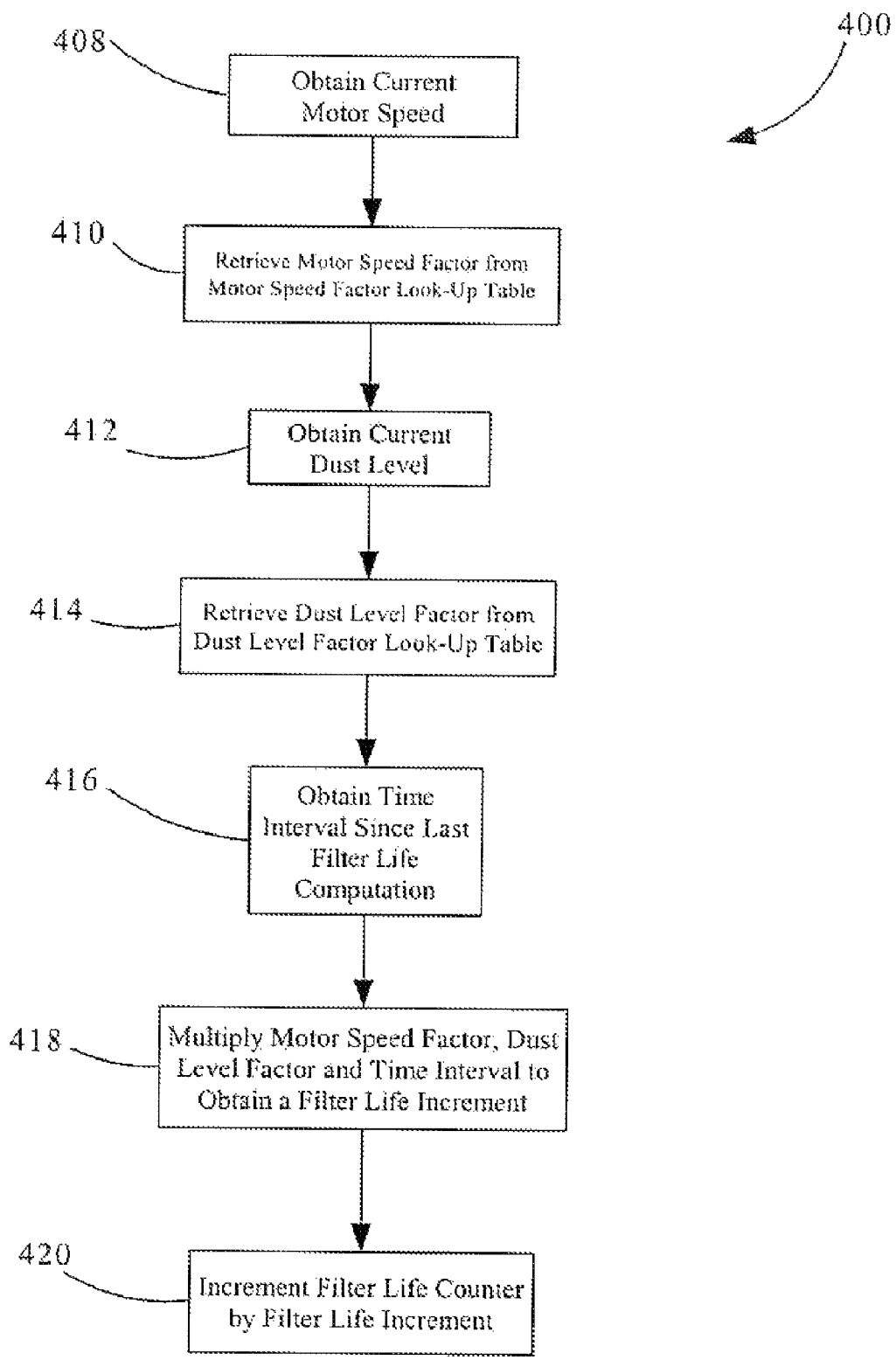
FIG. 7 is a flowchart showing the general steps of one embodiment of the filter life algorithm.

In one embodiment, the filter life algorithm for the particulate filter is somewhat more complex than the other filter life algorithms because it may take particulate sensor readings into consideration. The particulate filter life algorithm 400 shown in FIG. 7 includes the following general steps: (i) obtain motor speed value 408, (ii) retrieve corresponding motor speed factor from a particulate filter look-up table 410, (iii) obtain current particulate level value 412, (iv) retrieve corresponding particulate level factor from a look-up table 414, (v) obtain time interval 416, (vi) multiply motor speed factor, particulate level factor and time interval 418, (vii) increment filter life counter by product of motor speed factor, particulate level factor and time interval 420.

In another embodiment, the filter life algorithm for the particulate filter determines the total amount of particulate that has entered the filter and compares that to a predetermined limit. In the current filter used this limit is 160 grams. This limit can vary depending on the design of the filter and the application. The particulate filter life algorithm in this case includes the following general steps: (i) obtain motor speed value, (ii) obtain current particulate level value, (iii) use the particulate level value to calculate the particulate density (grams/cubic foot) or retrieve the particulate density from a look-up table, (iv) obtain time interval since the last calculation, (v) multiply motor speed, particulate density and time interval, (vi) increment filter life accumulator by product of motor speed, particulate density and time interval.

The filter life algorithm may take any of various predetermined actions once the filter life for a particular filter has exceeded a predetermined value. For example, the filter life algorithm may illuminate an LED or other indicator to advise the user that the filter needs to be changed. If the user fails to change the filter within a specific period of time, the filter life algorithm could prevent operation of the system.

The filter life algorithms are described in connection with an air treatment system having a particulate sensor. Accordingly, the particulate filter life algorithm takes into consideration the output of the particulate sensor. These algorithms are also well suited for using in taking into consideration other types of relevant input. For example, if the air treatment system included a chemical sensor, the odor filter life algorithm may take into account the output of the chemical sensor in essentially the same manner as the particulate filter life algorithm takes account of the particulate sensor output.

The above description is that of the current embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The embodiments of the invention in which an exclusive property or privilege is claimed are defined as follows:

1. A method for tracking filter life of a filter in an air treatment system, comprising the steps of:
   maintaining data indicative of a running time of a motor and a motor speed;
   comparing the maintained data to a predetermined value; and
   providing an indication to a user when the maintained data exceeds the predetermined value,
   wherein the step of maintaining data includes the steps of:

maintaining a variable representative of filter life;
obtaining a motor speed;
obtaining a value indicative of a characteristic of air being treated by the air treatment system;
obtaining a time interval;
multiplying the time interval by a value representative of the motor speed and a value representative of the characteristic of air being treated by the air treatment system to obtain an incremental value; and
incrementing the filter life variable by the incremental value.

2. The method of claim 1 wherein
the value representative of the motor speed is a motor speed factor obtained from a look-up table.

3. The method of claim 1
wherein the value indicative of a characteristic of air being treated by the air treatment system is a particulate level value, and
wherein the value representative of a characteristic of air being treated by the air treatment system is a value representative of the particulate level.

4. The method of claim 3 wherein
the value representative of the particulate level is a particulate level factor obtained from at least one of a formula and a look-up table.

5. The method of claim 1
wherein the value indicative of a characteristic of air being treated by the air treatment system is an input from a chemical sensor.

6. The method of claim 1 wherein the time interval is an interval that has passed since a last motor speed was obtained.

7. The method of claim 1 wherein the step of providing an indication to a user when the filter life variable exceeds the predetermined value includes illuminating a signal light.

8. The method of claim 1 wherein the air treatment system includes at least two of a pre-filter, a particulate filter and an odor filter, wherein the method includes maintaining separate filter life variables for each of the at least two filters.

9. The method of claim 1 including preventing operation of the air treatment system when the filter life variable exceeds the predetermined value for a predetermined amount of time.

10. A method for tracking filter life of a particulate filter in an air treatment system, comprising the steps of:
maintaining a filter life variable representative of filter life;
obtaining a motor speed;
obtaining a current particulate level;
obtaining a time interval since a previous calculation;
calculating an incremental value as a function of the motor speed, a value representative of the current particulate level and the time interval;
incrementing the filter life variable by the incremental value; and
providing an indication to a user when the filter life variable exceeds a predetermined value.

11. The method of claim 10 including the step of determining a value representative of the current particulate level; and
wherein the value representative of the current particulate level is a particulate density.

12. The method of claim 11 wherein the step of determining a value representative of the current particulate level includes at least one of calculating the particulate density as a function of the current particulate level and retrieving the particulate density from a look-up table as a function of the current particulate level.

13. The method of claim 10 wherein the step of providing an indication to a user when the filter life variable exceeds a predetermined value includes illuminating a signal light.

14. The method of claim 10 including preventing operation of the air treatment system when the filter life variable exceeds the predetermined value for a predetermined amount of time following said step of providing an indication to a user when the filter life variable exceeds a predetermined value.

15. The method of claim 10 wherein the air treatment system includes at least two of a pre-filter, a particulate filter and an odor filter, wherein the method includes maintaining separate filter life variables for each of the at least two filters.

16. A method for tracking filter life of at least three different filters in an air treatment system, comprising the steps of:
maintaining a first filter life variable representative of filter life for a first filter;
maintaining a second filter life variable representative of filter life for a second filter;
maintaining a third filter life variable representative of filter life for a third filter;
obtaining a motor speed;
obtaining a time interval since a last motor speed was obtained;
obtaining an input from a particulate sensor;
obtaining an input from a chemical sensor;
calculating a first filter life increment as a function of the motor speed and the time interval;
incrementing the first filter life variable by the first filter life increment;
comparing the first filter life variable to a predetermined first value;
providing a first indication to a user when the first filter life variable exceeds the predetermined first value;
calculating a second filter life increment as a function of the motor speed, the time interval and the input from the particulate sensor;
incrementing the second filter life variable by the second filter life increment;
comparing the second filter life variable to a predetermined second value;
providing a second indication to the user when the second filter life variable exceeds the predetermined second value;
calculating a third filter life increment as a function of the motor speed, the time interval and the input from the chemical sensor;
incrementing the third filter life variable by the third filter life increment;
comparing the third filter life variable to a predetermined third value; and
providing a third indication to a user when the third filter life variable exceeds the predetermined third value.

17. The method of claim 16 wherein at least one of providing a first indication, providing a second indication and providing a third indication includes illuminating a signal light.

18. The method of claim 16 including preventing operation of the air treatment system when at least one of the first filter life variable exceeds the predetermined first value for a predetermined first amount of time, the second filter life variable exceeds the predetermined second value for a predetermined second amount of time, and the third filter life variable exceeds the predetermined third value for a predetermined third amount of time.

* * * * *